(12) United States Patent
Bauer

(10) Patent No.: US 7,028,878 B2
(45) Date of Patent: Apr. 18, 2006

(54) STAPLING DEVICE FOR CLOSURE OF DEEP TISSUE

(76) Inventor: William Bauer, 80 Summerhill Pl., Newnan, GA (US) 30263

( * ) Notice: Subject to any disclaimer, the term of this patent is extended or adjusted under 35 U.S.C. 154(b) by 479 days.

(21) Appl. No.: 10/206,369

(22) Filed: Jul. 29, 2002

(65) Prior Publication Data

US 2003/0028218 A1    Feb. 6, 2003

Related U.S. Application Data

(66) Substitute for application No. 60/308,611, filed on Jul. 31, 2001.

(51) Int. Cl.
*A61B 17/04* (2006.01)
(52) U.S. Cl. .............. 227/175.1; 606/142; 606/220
(58) Field of Classification Search ............ 227/901; 606/51, 52, 39–149, 205–211
See application file for complete search history.

(56) References Cited

U.S. PATENT DOCUMENTS

| | | | |
|---|---|---|---|
| 4,394,864 A | 7/1983 | Sandhaus | |
| 4,569,346 A | 2/1986 | Poirier | |
| 4,997,436 A | 3/1991 | Oberlander | |
| 5,035,692 A * | 7/1991 | Lyon et al. | 606/143 |
| 5,293,863 A | 3/1994 | Zhu et al. | |
| 5,304,183 A | 4/1994 | Gourlay et al. | |
| 5,354,312 A * | 10/1994 | Brinkerhoff et al. | 606/207 |
| 5,456,400 A | 10/1995 | Shichman et al. | |
| 5,702,048 A | 12/1997 | Eberline | |
| 5,915,615 A | 6/1999 | Bauer | |
| 6,099,536 A * | 8/2000 | Petillo | 606/142 |
| 6,460,749 B1 * | 10/2002 | Levinson et al. | 227/180.1 |
| 6,582,451 B1 * | 6/2003 | Marucci et al. | 606/207 |

* cited by examiner

*Primary Examiner*—Glenn K. Dawson
(74) *Attorney, Agent, or Firm*—DLA Piper Rudnick Gray Cary US LLP

(57) ABSTRACT

A mechanical stapling device for fastening deep tissue during the closing of peritoneal side of a stab wound, which is associated with a laparoscopic surgical procedure, is provided. Also provided is a unique staple for use with the stapling device of the present invention. A method of using the device and staple of the present invention is also provided.

17 Claims, 5 Drawing Sheets

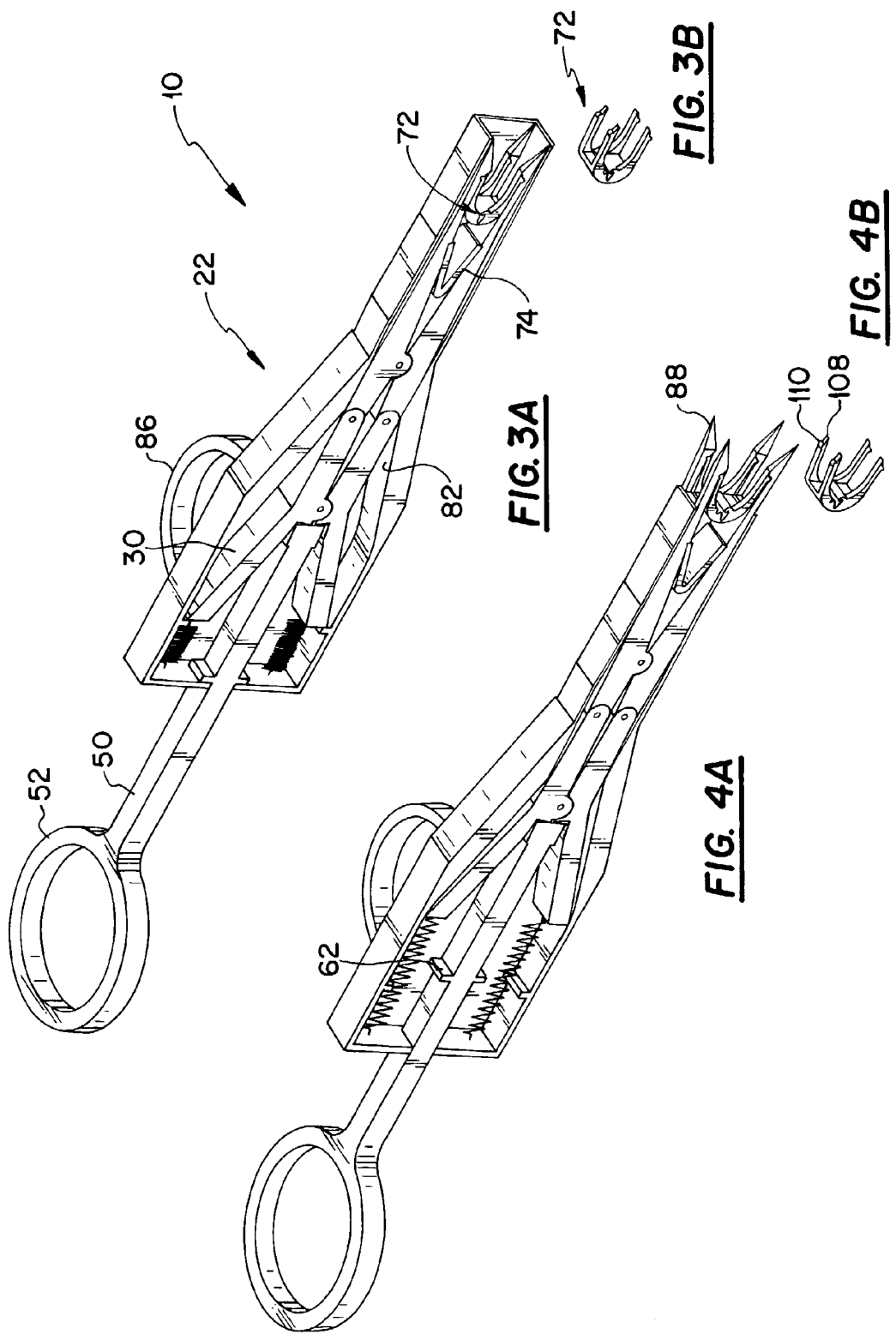

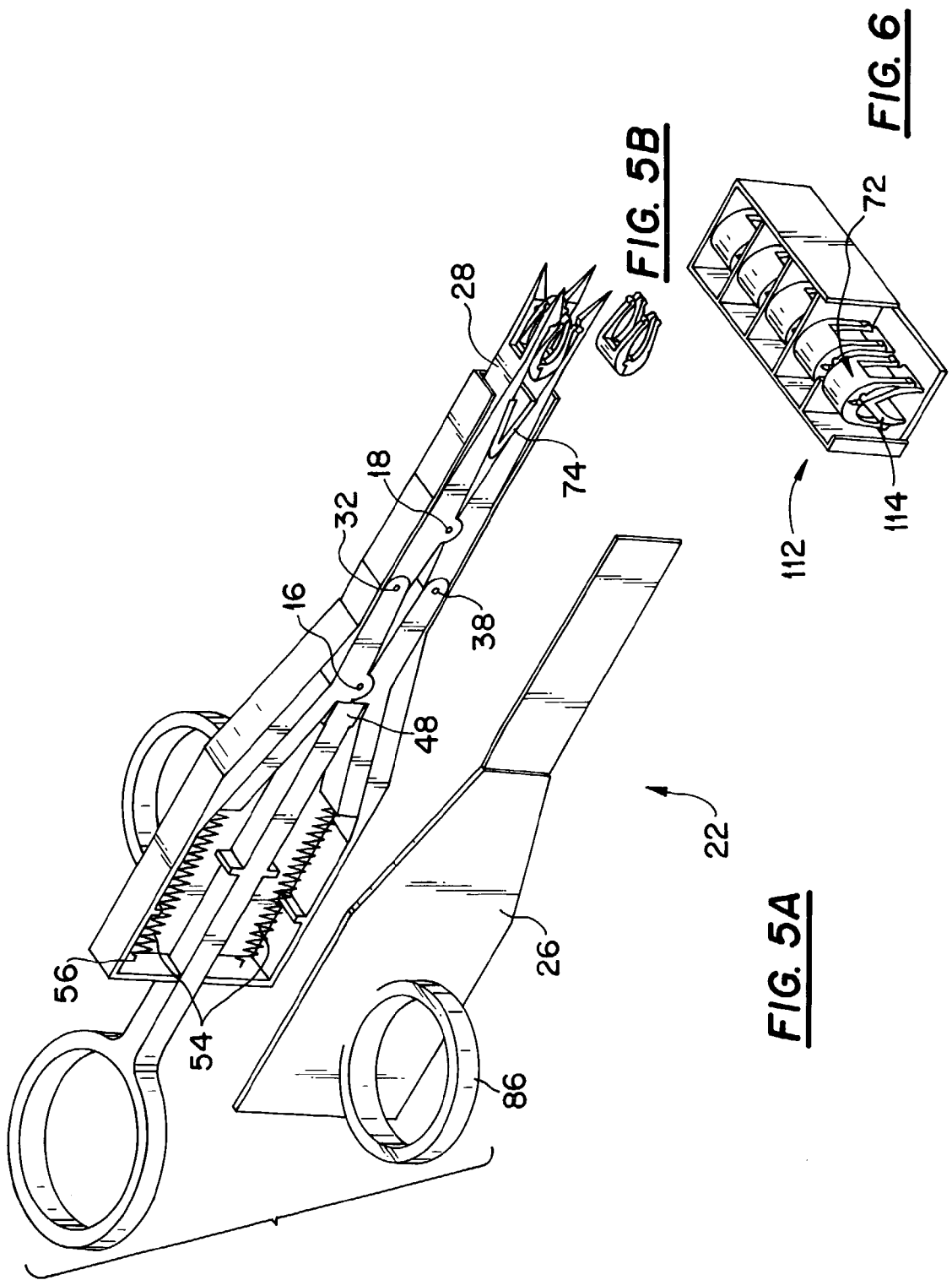

STAPLING DEVICE FOR CLOSURE OF DEEP TISSUE

This application claims the benefit of U.S. Provisional Application No. 60/308,611, filed Jul. 31, 2001.

BACKGROUND OF THE INVENTION

1. Field of the Invention

This invention relates to a device for fastening tissue during the process of a surgical procedure on a subject. More particularly the present invention is directed to a stapling device, which can be used to close the peritoneal side of a stab wound, which is associated with a laparoscopic surgical procedure.

2. Description of Related Art

The use of staples and staple insertion devices for the closure of surgical wounds to the skin and fascia of a subject are well known and used in the surgical arts. Laparoscopic surgical procedures have increased in number substantially over the past few years. However, the closure of wounds associated with laparoscopic procedures still primarily relies on conventional manual suturing methods. With more advances in surgical instrumentation the number of laparoscopic procedures done annually is estimated at over ten million a year in the United States alone. The instrumentation used for deep tissue closure of tissue at the conclusion of laparoscopic surgery remains the needle holder and suture. Although laparoscopic surgical procedures are minimally invasive using relatively thin trocars to penetrate into the abdominal cavity, the resulting openings or stab wounds, which are caused in the abdominal wall are extremely difficult to close upon completion of the surgery. Typically, the openings are approximately twelve millimeters in size and prove extremely awkward and time consuming to close using conventional suturing methods with traditional hand-held needle holders and suture. The use of this conventional methodology is difficult for the surgeon to properly accomplish and further is potentially hazardous for the surgical patient.

A growing number of postoperative complications in the form of hernias, which often require open closure, have been observed as the number of laparoscopic procedures has increased. Such postoperative problems are a result of not placing a deep stitch in the peritoneal side of the stab wound because of the difficulty associated with doing it or inadequately placing the suture needed to close the deep tissue of the wound. Incisions, which are smaller than the typical size of about twelve millimeters do not have a nearly so significant rate of complications.

While stapling devices have been designed and provided for other surgical procedures, none of the conventional surgical stapling devices are designed for the special requirements of deep tissue closure in laparoscopic procedures. A growing need exists for a stapling device which can be used to effectively penetrate the opposite sides of a deep wound and effect a suitable closure of the wound.

Currently used stapling devices are well suited to the particular needs for which they were designed but are hardly adaptable for use in deep tissue closure following laparoscopic surgery. U.S. Pat. No. 5,915,615, issued to Bauer, discloses a manually operated fastening device for use in meeting the specialized requirements of fastening septal tissue within the narrow passages of the nose during septal surgery. While this fastening device is effective for fastening septal tissue it would be unsuitable for the requirement for a deep tissue stapling device described in the present application. Another specialized instrument is disclosed in U.S. Pat. No. 4,394,864 issued to Sandaus, which discloses a vas occlusion device that includes jaw members for holding open a locking clip and for penetrating tissue in which the clip is to be closed. Both of these prior art devices adequately meet the specific needs for the surgical procedures, which are discussed in their disclosures but fail to provide an adequate substitute for the currently used needle holder and suture. For this reason, surgeons today continue to manually suture the deep tissue of a laparoscopic surgical wound.

Another well known mechanical surgical fastening device is taught in U.S. Pat. No. 4,997,436 issued to Oberlander. The Oberlander patent is directed to an arthoscopic clip insertion device with jaws that hold a biodegradable clip, the jaws having sharpened tips to facilitate insertion of the clip into soft tissue or fibrocartilage. U.S. Pat. No. 5,456,400 issued to Schichman et al., discloses a surgical fastener that has pre-piercing members that penetrate body tissue to facilitate insertion of a clip therein and to close the clip. Another example of a conventional fastening or clipping device which is well known in the surgical arts but which is equally wholly unsuited to the need for a deep tissue closure device is taught by U.S. Pat. No. 4,569,346 issued to Poirer. The Poirer apparatus is an occluding device for applying two clips and cutting the tissue positioned there between. None of the conventional stapling, fastening, or clipping devices currently known and used in the surgical art are capable of effectively and consistently performing closure of deep tissue following laparoscopic surgery.

The conventional procedure for manually suturing the peritoneal side of a laparoscopic surgical wound has proven to be inadequate to avoid the many complications that increasingly present post surgically. None of the conventional mechanized stapling devices, as represented by the selected U.S. Patents discussed above, teach or suggest an instrument that could adequately meet the need for an effective and safe stapling device for use in closing the peritoneal side of a laparoscopic surgical wound. The inventor has designed the present invention to meet that very particular requirement.

SUMMARY OF THE INVENTION

In accordance with the principles of the present invention, a stapling device, which is designed to place and attach an absorbable self-locking, suture clip or staple for closure of the peritoneal side of a stab wound is provided. The device of the present invention, satisfies the long felt need for a mechanized, dependable, and safe procedure for fastening the deep tissue of a laparoscopic stab wound at the conclusion of the surgical procedure.

The present invention offers clear advantages over the conventional use of suturing material applied with needle holders. The consistent and complete closure of the wound using the apparatus and method of the present invention is far superior to the historically inadequate use of conventional manual suturing of the peritoneal side of a laparoscopic stab wound. Additionally, the patients for whom the present invention is used would not be subject to the occurrence of hernia and infection, which often accompanies inadequate closure of deep tissue following laparoscopic surgery.

Thus it is an object of the present invention to provide a mechanical stapling device for closure of the peritoneal side of a stab wound associated with laparoscopic surgery. More particularly, it is an object to provide such a device, which positions, inserts, and secures absorbable fasteners or staples in the deep tissue of a laparoscopic stab wound.

It is another object of the present invention to provide a staple that is configured for use with the stapling device of the present invention. More particularly it is the object of invention to provide an absorbable staple for use in deep tissue closure for a laparoscopic stab wound. A cartridge which facilitates the storage and loading of such staples is also provided.

It is another object of the present invention to provide a method for using the stapling device and staple of the present invention to effectively close the peritoneal side of a laparoscopic stab wound.

BRIEF DESCRIPTION OF THE DRAWINGS

FIG. 3A shows a perspective view of the deep tissue closure device with a staple in place within the device and the second mating part of the housing removed to reveal the interior mechanism of the device. This view shows the distal portion of the upper arm assembly fully retracted within the housing of the device. FIG. 3B shows the configuration of a staple as it would appear contained within the deep tissue closure device of FIG. 3A.

FIG. 4A shows a perspective view of the deep tissue closure device with a staple in place within the device and the second mating part of the housing removed to reveal the interior mechanism of the device. This view shows the distal portion of the upper arm assembly extended distally from the confines of the housing in a configuration for insertion of the staple into the deep tissue of a laparoscopic stab wound. FIG. 4B shows the configuration of a staple as it would appear held in the deep tissue closure device of FIG. 4A.

FIG. 5A shows a perspective view of the deep tissue closure device with a staple in place within the device and the second mating part of the housing removed to reveal the interior mechanism of the device. This view shows the distal portion of the upper arm assembly extended distally from the confines of the housing in a configuration for attachment into and closure of the deep tissue of a laparoscopic stab wound. FIG. 5B shows the configuration of a staple as it would appear held in the deep tissue closure device of FIG. 5A.

FIG. 6 shows a collection of staples for use in the deep tissue closure device of the present invention, the collection being contained in a cartridge which can facilitate the insertion of the staples into the closure device.

DETAILED DESCRIPTION OF THE INVENTION

Figure 1:
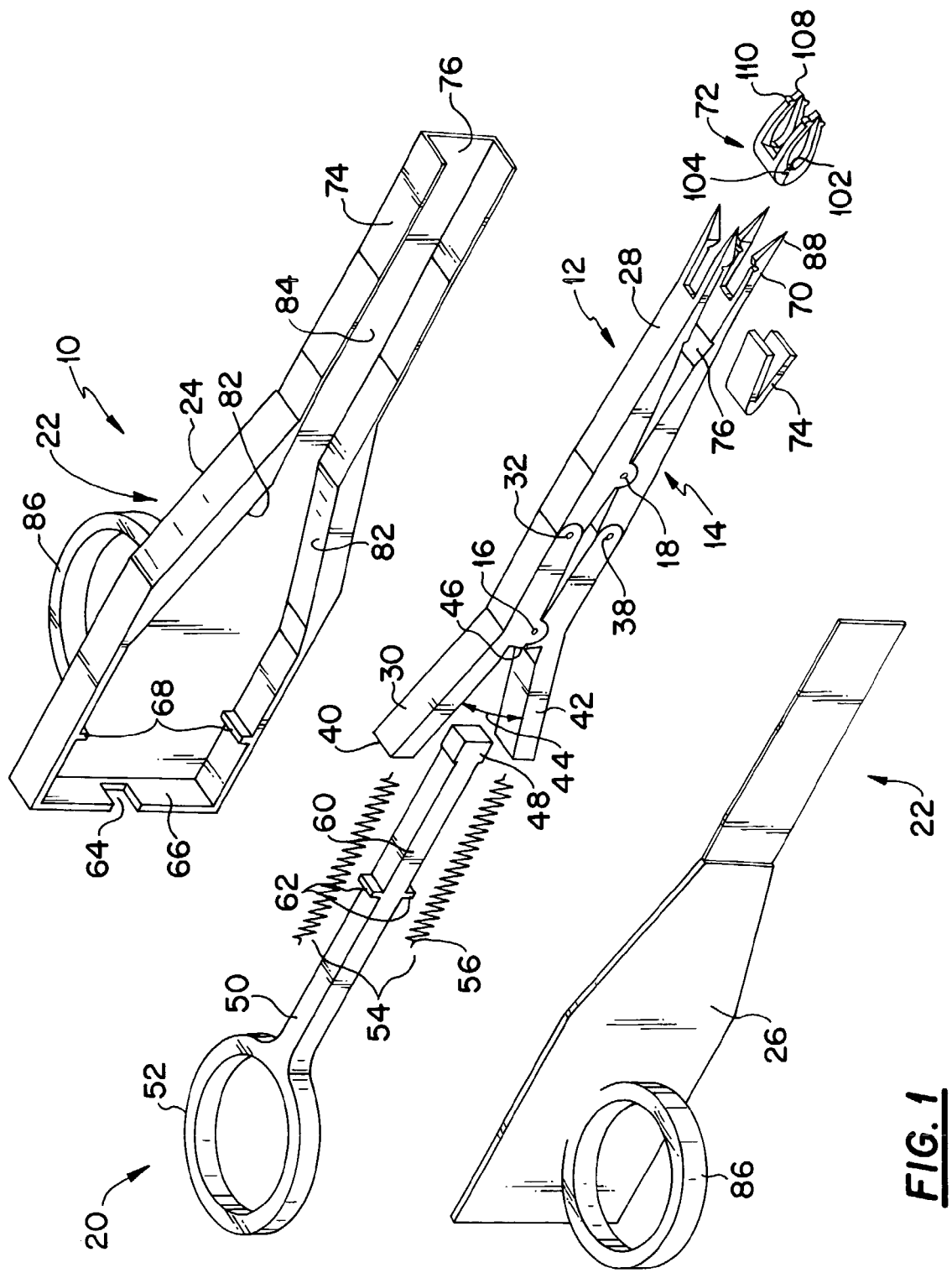
FIG. 1 is an exploded perspective view of the deep tissue closure device embodying the principles of the present invention.

The present invention is described below with reference to FIGS. 1–7D. The following description and the related figures are provided as non-limiting examples, which embody the principles of the invention described herein and as claimed by the inventor.

The deep tissue stapling device of the present invention 10 includes an upper arm assembly, generally indicated at 12 and a lower arm assembly, generally indicated at 14. The lower arm assembly 14 is disposed below and connected to the upper arm assembly 12 at a proximally disposed first pivot joint 16 and a distally disposed second pivot joint 18. Moveably connected to the upper and lower arm assemblies (12 and 14) at a position adjacent to the proximal side of the first pivot joint 16 is an actuator, generally shown at 20. A housing assembly, generally shown at 22 includes a first mating part 24 and a second mating part 26, which when mated to form the housing assembly 22 serve to provide an enclosure for a major portion of the mechanism of the stapling device 10.

As best shown in FIGS. 1 and 2A–C, the upper arm assembly 12 includes an upper arm assembly distal end 28 pivotally connected to an upper arm assembly proximal end 30 by an upper arm assembly pivot joint 32. In a similar configuration, the lower arm assembly 14 includes a lower arm assembly distal end 34 pivotally connected to a lower arm assembly proximal end 36 by a lower arm assembly pivot joint 38. The terminal portion 40 of the proximal end 30 of the upper arm assembly 12 and the terminal portion 42 of the proximal end 36 of the lower arm assembly 14, which are disposed proximate to the first pivot joint 16 are angled away from each other so as to define a y-shaped angular space 44 there between. An actuator abutment 46 is formed by the most proximal surfaces of the first pivot joint 16, The acutator abutment 46 defines the distal limit of the y-shaped space 44. The actuator abutment 46 is sized and configured to receive moving contact from the distal end 48 of the actuator 20. A proximal portion 50 of the actuator 20 extends proximally outside of the housing assembly 22. The proximal portion 50 can be configured with a manual control member 52, which can be manipulated by a user to move the actuator 20 during operation of the stapling device 10. A preferred configuration of the manual control member 52 is a thumb or finger hole defined within the proximal portion 50 of the actuator 20. However, any configuration of the control member 52, which facilitates movement of the actuator 20 is within the concept of the invention. It is also possible to augment the movement of the control member 52 by use of a spring biased trigger mechanism or other automated augmentation device without departing from the concept of the present invention.

Figure 2A:
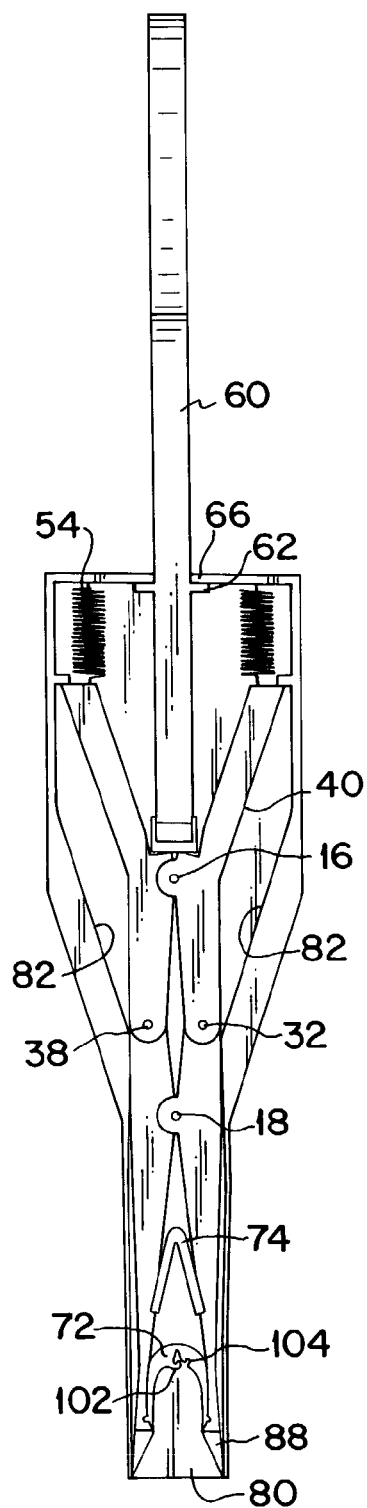
FIGS. 2A, 2B, and 2C show in progression of use, the three primary positions of the deep tissue closure device of the present invention.
Figure 2B:
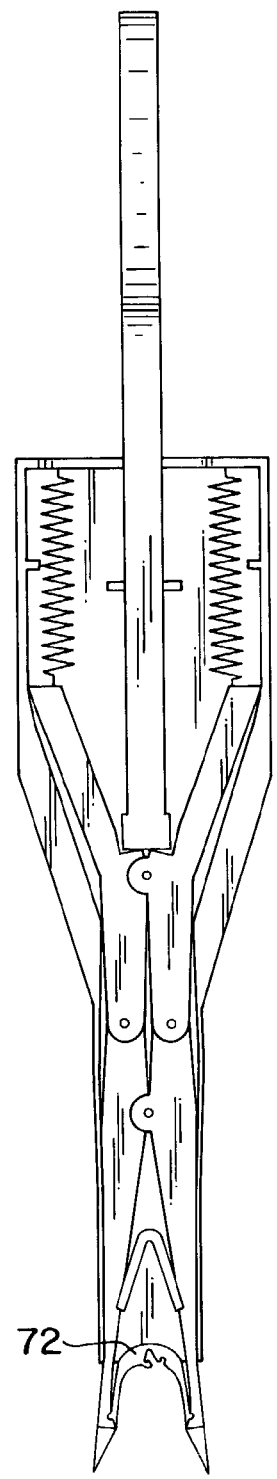
Figure 2C:
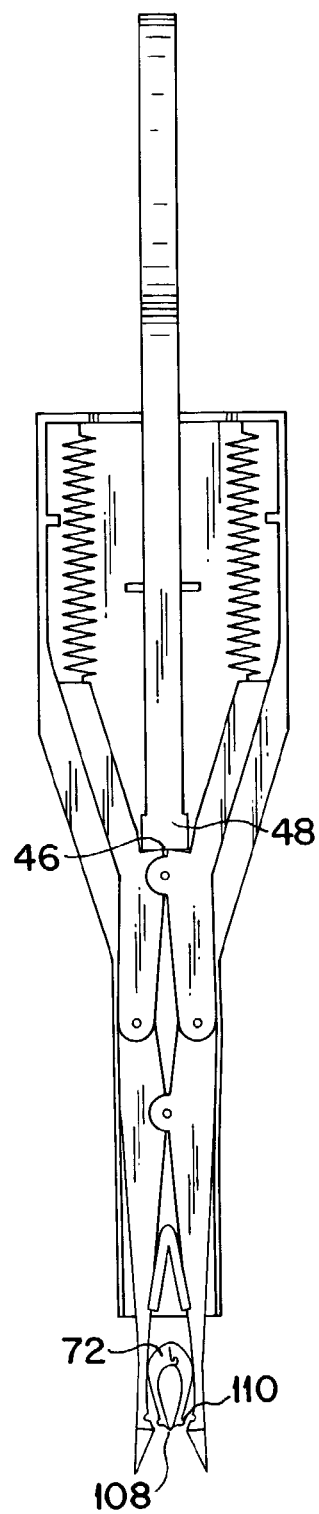

As best shown in FIGS. 2A–C, when in use, the user initiated manual movement of the actuator 20 in a distal direction results in the actuator proximal portion 50 contacting and distally repositioning the actuator abutment 46 within the housing assembly 22. Distal movement of the pivotally connected upper and lower arm assemblies 12, 14 is against a bias, which is exerted by at least one arm assembly biasing member 54. The arm assembly biasing member can be a spring, band, piston, or other equivalent structure which serves to exert a bias to retain the moveable arm assemblies in a retracted position, that is a proximally oriented position, within the housing assembly 22. The arm assembly biasing member can be either a pushing or pulling force to exert a bias on the moveable arm assembly. A non-limiting example of a biasing member is at least one spring longitudinally aligned with the arm assemblies 12, 14; the spring being connected at a first end 56 to the proximal end of the housing assembly 22 and connected at a second end 58 to the proximal end of the terminal portions 40, 42 of the arm assemblies 12, 14. A reversal of the bias to push the arm assemblies in a proximal direction is also within the concept of the present invention.

The proximal portion of the actuator 50 is connected to the distal end of the actuator by an actuator shaft 60. An actuator retainer 62 is positioned on the actuator shaft 60 at a select position for the purpose of limiting the proximal movement of the actuator shaft 60. The actuator shaft 60 is sized and configured to slidably pass through a shaft access port 64, which is defined in a proximal wall 66 of the housing assembly 22. The shaft access port 64 is sized to allow free sliding movement of the actuator shaft 60 into the housing in response to the manual movement of the actuator by a user and it is sized to allow free sliding movement of the actuator shaft 60 proximally out of the housing assembly 22 in response to the rearward bias exerted by the arm assembly biasing member 54. The shaft access port 64 and the actuator retainer 62 are comparatively sized such that the outward movement of the actuator shaft 60 is stopped when the larger sized actuator retainer 62 abuts against the smaller sized shaft access port 64. This configuration of the actuator shaft 60 and the shaft access port 64 serves to retain the distal portion of the actuator 20 within the confines of the housing assembly 22 when the actuator 20 is moved proximally as the arm assemblies 12, 14 push rearward against the actuator due to the bias exerted by the arm assembly biasing member 54.

The interior walls of the housing assembly 22 can be provided with at least one arm assembly retainer 68, which is connected to and positioned within the housing assembly so as to block excessive movement of the upper and lower arm assemblies 12, 14. The arm assembly retainer 68 is configured and positioned to permit rearward movement of the connected upper and lower arm assemblies 12 and 14 in response to the arm assembly biasing member to the extent that the distal ends 28, 30 of the arm assemblies 12, 14 are fully retracted within the housing assembly 22. The arm assembly retainer 68 can be positioned within the housing so as to act as a block when the proximal or rearward movement of the proximal ends 40, 42 of the arm assemblies 12, 14 strike against the retainer 68. While this configuration is preferred, the scope of the present invention permits the positioning of the arm assembly retainer 68 anywhere within the device that the blocking effect on the arm assemblies 12, 14 can be accomplished.

The opposing surfaces of the distal ends 28, 34 of the upper and lower arm assemblies 12, 14 are provided with a staple retention seat 70, which is sized and configured to releasably retain a staple, generally shown at 72. Proximate to the staple retention seat 70 is an outward biasing member 74, which is positioned in a bias member seat 76 defined in the opposing surfaces of the distal ends 28, 34 of the arm assemblies 12, 14. The outward biasing member 24 exerts an outward bias to keep the distal ends 28, 34 of the arm assemblies 12, 14 apart from each other unless forcibly brought together. The housing assembly 22 at its most distal end 78 defines an arm assembly exit portal 80 through which the distal ends 28, 34 of the arm assemblies 12, 14 can be extended outwardly in response to a user moving the actuator 20 into the housing assembly 22.

During operation of the present invention, the movement of the actuator 20 into the housing assembly 22 forces the actuator distal end 48 to drive against the actuator abutment 46, which forces the connected arm assemblies 12, 14 to move distally along the longitudinal axis of the housing assembly 22 until the terminal portions 40, 42 of the arm assemblies 12, 14 contact the inner contact surfaces 82 of the housing assembly 22. This distal movement of the arm assemblies 12, 14 serves to move the distal ends 28, 32 of the arm assemblies outwardly from the confines of the housing assembly 22 through the arm assembly exit portal 80.

As best shown in FIGS. 2A–C the pivotally connected arm assemblies 12, 14 as they are force distally through the arm assembly channel 84, which is defined by the walls of the housing assembly 22, effect a scissors action in relation one to another. The effect of this scissors action combined with the outward bias of the biasing member 74 is to force the distal ends 28, 32 of the arm assemblies to open as the distal ends 28, 32 pass out through the exit portal 80.

As best shown in FIG. 2B the staple 72, which is removably seated between the distal ends 28, 32 of the arm assemblies, is permitted to expand to a more open configuration as the distal ends 28, 32 open during the process passing outwardly through the exit portal 80. The staples are formed with a bias to an open position and for that reason naturally tend to follow the opening movement of the distal ends 28, 32 of the arm assemblies 12, 14.

FIG. 3A shows an exposed view of the device prior to movement of the actuator by a user. The arm assembly biasing members 54, shown for demonstration purposes as springs, are in a coiled or relaxed state, while the arm assemblies and the seated staple are fully housed within the housing assembly 22. FIG. 3B shows the configuration of the staple as it would be in the device shown in FIG. 3A. The staple, as it would be in the device shown in FIG. 3A is open but not fully opened to its biased configuration.

FIG. 4A shows an exposed view of the device after distally directed movement of the actuator has begun but prior to completion of such distal movement of the actuator when the terminal portions 40, 42 of the proximal ends of the arm assemblies 12, 14 contact the inner contact surfaces 82 of the housing assembly 22. FIG. 4B shows the configuration of the staple as it would be in the device shown in FIG. 4A. The distal ends 28, 34 of the arm assemblies are extended outwardly from the arm assembly exit portal and as discussed above are opened in response to the force exerted by the outward biasing member 74. The staple shown in FIG. 3B is configured in an open position in response to it's inherent bias to an open configuration and as allowed by the open position of the distal ends 38, 42 shown in the device of FIG. 4A.

Figure 7A:
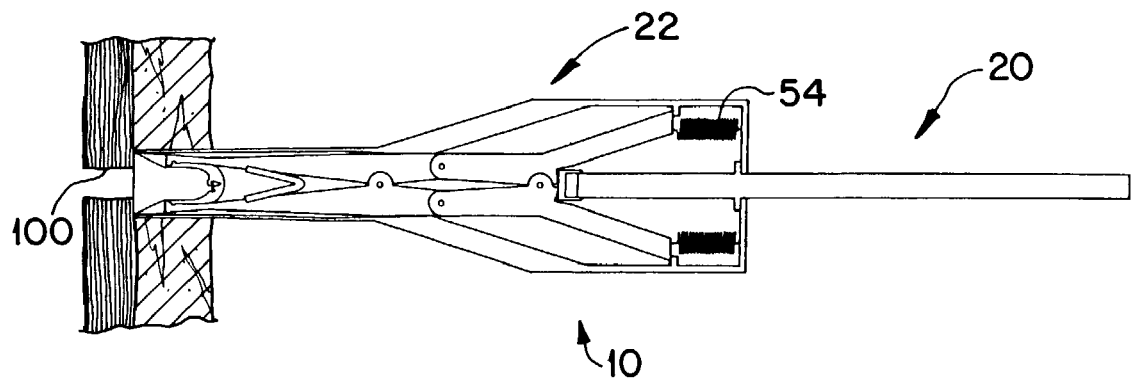
FIGS. 7A, 7B, and 7C show the interior mechanism of the deep tissue closure device of the present invention and a staple for use therewith in the same configurations depicted in FIGS. 2A–C. Also shown is a graphic depiction of a laparoscopic stab wound as it would be entered and closed using the present invention.
Figure 7B:
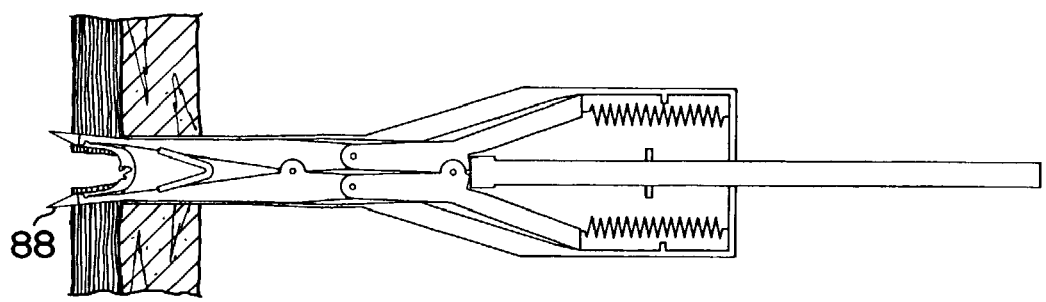

It is in the configuration shown in FIG. 4A that the user would manually manipulate the device 10 into a staple insertion position by holding the housing assembly 22. At least one housing grip 86 is provided on the external surface of the housing assembly to facilitate a secure manual gripping of the device 10 by a user during any manipulation or operation. Preferably, the housing grip can be a finger hole defined by an integrally formed extension of the housing assembly; however, any addition to the housing assembly which would improve the manual grip of a user during operation of the device is included within the concept of the present invention. Having manually placed the device into a position where the outwardly extended distal ends 38, 42 of the arm assemblies 12, 14 are directly adjacent the peritoneal side of a stab wound, the tissue entry elements 88 of the distal ends 28, 32 can be manually forced into the deep tissue, which is to be closed by the device 10. FIGS. 7A–B best show the method of positioning the device and forcing entry of the elements 88 into the deep tissue of the subject. As shown in FIG. 7B the staple 72, which is held within the staple retention seat 70 is also carried into the deep tissue 100 of the subject as the device is manipulated by the user during the insertion step of the process. As earlier indicated it is within the scope of the present invention to provide an augmentation force, such as a spring and trigger release to assist in the insertion and closure of the staple 20.

Figure 7C:
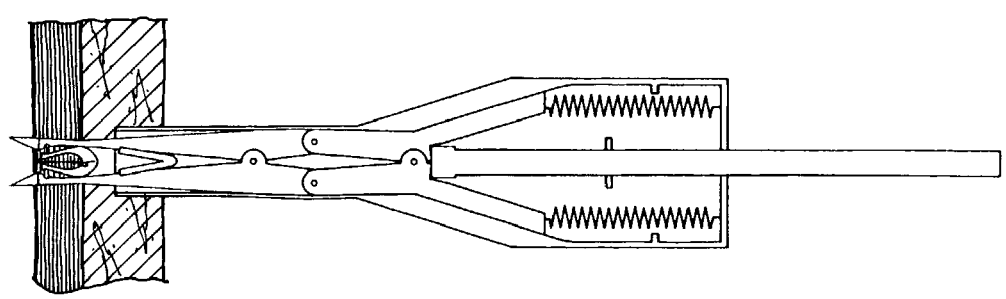
Figure 7D:
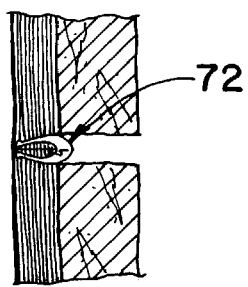
FIG. 7D shows the staple inserted and locked in the closed position following the use of the stapling device to close deep tissue in a stab wound.

As best shown in FIG. 5A, the actuator can be fully displaced distally so as to force the terminal portions 40, 42 against the inner contact surface 82 of the housing assembly 22. When this contact is made, the configuration of the arm assemblies 12, 14 is such that the y-shaped angular space 44 defined by the terminal portions 40,42 is minimized. In this configuration, the scissors action of the pivotally connected arm assemblies 12, 14 as influenced by the restrictions of the arm assembly channel 84 acts to compress the outward biasing member 74 and draw the distal ends 38, 42 together. The effect of drawing the distal ends 38, 42 together is to compress the staple 72 into a closed and locked position as shown in FIG. 2C. A locking member 102 located on one arm of the staple 72 is securely connected to a lock receptor 104 located on the opposing arm of the same staple 72. A preferred embodiment of the locking member 102 and the lock receptor 104 are a male and female configuration as depicted in FIGS. 2A–C. This male-female configuration can be modified to have a securing hook 106 on the terminal portion of the locking member 102; however, any locking device which will facilitate a secure closure and locking of the staple 72 is within the concept of the present invention. The staple 72 is also provided with at least one staple point 108 which facilitates insertion of the staple into the tissue of a subject. Also clearly shown in FIG. 5B is the staple retention seat locking nub 110, which is configured to hold the staple in place in the staple retention seat 70 prior to closure by the device 10 and release therefrom. FIG. 5B shows the staple as used in the device of FIG. 5A and as found in a closed and locked configuration. FIG. 7C shows the device of FIG. 5A as it is used in relation to the deep tissue to be closed by the device. It can be seen that the staple 72 shown in FIG. 7C has approximated the edges of the deep tissue into a secure and closed condition. FIG. 6 shows a cartridge 112 containing staples 72 for use with the device 10. The cartridge 112 can have any configuration which provides protection and ease of access for purposes of extracting staples 72 to be used in the device 10. The embodiment of a cartridge 112 shown in FIG. 6 includes a staple holder 114, which is configured to hold the staples 72 in the proper position for easy insertion into the device 10. The benefit of the present invention is the ease of use, the consistency of results, and the improved safety of the device for closing deep tissue stab wounds.

After positioning, inserting, closing and locking the device 10 and staple 72 of the present invention, the user can easily extract the device 10 from the stab wound and proceed to close the remaining superficial tissues by other means known in the surgical arts.

It can be appreciated that the deep tissue stapling device 10 of the present invention permits relatively large bioabsorbable fasteners to be delivered through a small entrance (a laparoscopic stab wound), to the peritoneal side of that stab wound for the purpose of effecting consistent, safe closures of the deep tissue following laparoscopic surgery. Although in the illustrated embodiment, the staple has two depending legs, it can be appreciated that a single-legged or multiple-legged staple can be retained with an associated receptacle.

While the invention has been described in connection with what is presently considered to be the most practical and preferred embodiment, it is to be understood that the invention is not limited to the disclosed embodiment, but, on the contrary, is intended to cover various modifications and equivalent arrangements included within the spirit and scope of the appended claims. For example, although the device has been disclosed for closure of deep tissue in a laparoscopic stab wound, the device of the invention could be used for fastening other structures during other surgical procedures as well.

What is claimed is:

1. A stapling device comprising:
    first and second arm assemblies, each of said arm assemblies having a distal portion and a proximal portion, said first arm assembly being in longitudinal alignment with and pivotally coupled to said second arm assembly by at least one pivot joint;
    an actuator having a proximal portion and a distal portion, said distal portion being sized and configured to pass along the longitudinal axis of said pivotally connected arm assemblies and between said proximal portions of said arm assemblies, said proximal portions of said arm assemblies being angled away one from the other so as to permit movement of said distal portion of said actuator there between up to an abutment defined by said pivotal connection of said arm assemblies;
    a staple seat defined in each of said distal portions of said arm assemblies, said staple seat in each of said arm assemblies being located facing toward and in opposition to the other of said staple seats.

2. The stapling device according to claim 1, wherein said at least one pivot joint comprises a first pivot joint and a second pivot joint spaced apart one from the other along the longitudinal axis of said arm assemblies.

3. The stapling device according to claim 2, further comprising:
    a first arm assembly pivot joint connecting said proximal and distal portions of said first arm assembly, said first arm assembly pivot joint being positioned between said first and second pivot joints along the longitudinal axis of said first arm assembly; and
    a second arm assembly pivot joint connecting said proximal and distal portions of said second arm assembly, said second arm pivot joint being positioned between said first and second pivot joints along the longitudinal axis of said second arm assembly, said first arm assembly pivot joint and said second arm assembly pivot joint being positioned approximately one above the other in the pivotally connected first and second arm assemblies.

4. The stapling device according to claim 3, further comprising a housing assembly surrounding a portion of said actuator and said proximal portions of said first and second arm assemblies.

5. The stapling device according to claim 4, wherein said housing assembly defines a shaft access port at a proximal end of said housing through which a portion of said actuator can slidably pass.

6. The stapling device of claim 5, wherein said housing assembly surrounds a portion of said distal portion of each of said arm assemblies, a distal end of said housing assembly defining an arm assembly exit portal, said exit portal being sized and configured to permit slidable passage of said distal portion of said arm assemblies.

7. The stapling device of claim 6, further comprising an outward biasing member positioned between and in contact with the opposing surfaces of each of said distal portions of said arm assemblies; said outward biasing member configured to exert a force biasing each of said distal portions of said arm assemblies apart one from the other.

8. The stapling device of claim 7, wherein said outward biasing member is a leaf spring positioned proximal to said staple seat.

9. The stapling device of claim 8, wherein a distal portion of said housing assembly defines an arm assembly channel, said channel being sized and configured to permit slidable passage of a distal portion of the pivotally connected arm assemblies, said channel terminating at said arm assembly exit portal.

10. The stapling device of claim 9, wherein said housing assembly comprises an inner contact surface configured to limit distally directed movement of said first and second arm assemblies, said arm assemblies being limited to movement to the extent that only said distal portion of said arm assemblies is permit to pass outward from said arm assembly channel through said exit portal.

11. The stapling device of claim 8, wherein each distal portion of said arm assemblies terminates in at least one tissue entry element, said tissue entry element being configured to permit ease of entry of said entry element into the tissue of a subject.

12. The stapling device of claim 11, wherein said at least one arm assembly biasing member comprises two springs, each of said springs having a first end and a second end; wherein said first end of each of said springs is attached to an inner wall of a proximal portion of said housing assembly and said second end of each of said springs is attached to a respective proximal portion of said first arm assembly or said second arm assembly.

13. The stapling device of claim 12 in combination with a staple sized and configured for use in said stapling device.

14. A method for stapling tissue in a subject, said method comprising:

providing a stapling device as claimed in claim 13;

positioning said stapling device with a wound requiring deep tissue closure;

distally displacing the actuator of said stapling device so as to insert, close, and release said staple; and removing said device from said wound.

15. The stapling device of claim 6, wherein said housing assembly is connected to said proximal portion of at least one of said arm assemblies by at least one arm assembly biasing member, said arm assembly biasing member being positioned so as to exert a force which draws said arm assembly in a proximal direction relative to said housing assembly.

16. The stapling device of claim 6, wherein said housing comprises a first mating part and a second mating part.

17. The stapling device of claim 16, further comprising an integrally formed housing grip on each of said first mating part and said second mating part.

* * * * *